United States Patent [19]

Buma et al.

[11] Patent Number: 4,689,079
[45] Date of Patent: Aug. 25, 1987

[54] METHOD OF PREPARING IMPRESSION TAKING AND MOLDING MATERIALS AND DENTAL DIAGNOSING/TREATING CHEMICAL MATERIALS USED IN THE METHOD

[75] Inventors: Mitsuo Buma, Kawagoe; Sadayuki Yuda, Suita; Masatsune Sato, Matsudo; Mitsuo Okada, Sayami, all of Japan

[73] Assignee: Sankin Kogyo Kabushiki Kaisha, Osaka, Japan

[21] Appl. No.: 796,937

[22] Filed: Nov. 12, 1985

[30] Foreign Application Priority Data

Nov. 12, 1984 [JP] Japan ................. 59-238071

[51] Int. Cl.$^4$ .............. C09K 3/00; A61K 6/10; C08L 5/04
[52] U.S. Cl. ................ 106/35; 106/129; 106/208; 106/38.51; 523/109; 524/28
[58] Field of Search ............. 106/35, 129, 38.5, 208; 523/109; 524/28

[56] References Cited
U.S. PATENT DOCUMENTS

| 2,756,874 | 7/1956 | Erickson et al. | 229/72 |
| 4,221,601 | 9/1980 | Augustin et al. | 106/186 |
| 4,381,947 | 5/1983 | Pellico | 106/38.51 |
| 4,515,913 | 3/1985 | Pellico | 106/35 |
| 4,569,954 | 2/1986 | Wilson et al. | 106/35 |

Primary Examiner—Theodore Morris
Attorney, Agent, or Firm—Handal & Morofsky

[57] ABSTRACT

Powder of chemical material for impression taking and molding for teeth is previously packed with a water-soluble film in an amount determined by each clinical treatment. A desired impression taking or molding material is obtained by putting such pack or packs in a proper amount of water and properly kneading them.

9 Claims, 2 Drawing Figures

METHOD OF PREPARING IMPRESSION TAKING AND MOLDING MATERIALS AND DENTAL DIAGNOSING/TREATING CHEMICAL MATERIALS USED IN THE METHOD

BACKGROUND OF THE INVENTION

1. Field of the Invention

The present invention relates to a method for preparing impression taking and molding materials by mixing and kneading chemical material powder with a proper quantity of water for dental diagnosis and treatment, and to dental chemical materials used in the method.

2. Description of the Prior Art

The chemical materials include dental alginate impression material (alginic acid salt), dental plaster, dental filling and restoration material known as a trademark "IONODENT" manufactured by Sankin Kogyo Kabushiki Kaisha (a mixture of carboxylic acid polymern and aluminosilicate) and dental cement, the selection and amount of which are determined according to each clinical case.

These materials have a property of being made plastic when mixed with water and become harder with time. Therefore, when it is desired to take patient's tooth impression with use of, for example, the alginate impression material, the quantity of the impression material powder required for the clinical treatment is conventionally measured with a measuring cup, and then the measured material powder and a proper amount of water are mixed and kneaded to a desired state suitable for the impression taking or impression molding. The quantity of the alginate impression material is prescribed to be 21, 14 and 7 grams for 1, ½ jaws and 2-3 teeth, respectively, while the powder measuring cup is designed for measurement of the minimum unit, in this case, 7 grams. When an impression of one jaw is to be taken, the cup is used three times to obtain the desired amount of the impression material powder, then the measured material is mixed with a proper quantity of water. The other chemical materials are prepared in the same manner.

As described above, prior to preparation of dental impression taking or molding material, a measuring tool such as the aforementioned cup must have been used to measure the chemical material of the amount necessary for respective clinical treatment. Thus, the conventional preparing method has many problems including the followings:

(1) Measurement of powder is troublesome and time-consuming.

(2) During such measurement, powder tends to fly off in different directions, which leads to an unhygienical examination room and powder loss.

(3) Since such chemical powder is usually stored in a container such as a can or a bag, some powder tends to remain in the bottom of the container as waste powder.

(4) Each measurement is not always accurate, and thus the ratio of mixture of the material to water is frequently inaccurate, which leads to a low impression taking or molding accuracy.

(5) The impression material and measuring tools must be maintained clean. In other words, they tend to be insanitary.

SUMMARY OF THE INVENTION

An object of the present invention is to provide a method of preparing impression taking and molding materials quickly and hygienically, and dental diagnosing/treating chemical materials used in the method.

Since the above problems result from the fact that chemical material powder must be measured for each clinical treatment, they can be solved by previously wrapping a predetermined amount of the chemical material powder in unit with water-soluble film. When it is so desired as to take or mold an impression of teeth in dental diagnosis and treatment, desired impression taking or molding material can be easily obtained merely by immersing the wrapped chemical material powder in a proper amount of water and then mixing and kneading them. Such watersoluble film may be made of polyvinyl alcohol (PVA), polysaacharide such as glucan, gelatine, cellulose or the like which are all well known and have been confirmed that no bad influence is exerted not only on human body but also on the intended properties of the impression taking or molding material. The amount of chemical material powder to be wrapped in one pack may b determined to be equal to the amount required for each clinical treatment or to the minimum use unit for each chemical material. In either case, by previously wrapping a certain amount of chemical material, such powder measurement as mentioned above will become unnecessary. Especially in the former case, a user, i.e., a dentist or a dental mechanic can quickly prepare a desired impression taking or molding material only by selecting a pack of material powder containing an amount corresponding to the clinical treatment. In the latter case, on the other hand, a certain number of packs must be used depending on the clinical treatment. However, a quantity of chemical material to be wrapped in one pack for respective chemical materials can be standardized. Therefore, the latter case has such advantages that (1) a maker can make the packs on mass production basis, (2) a user can readily control packs in stock by checking the total number and (3) both user and maker are beneficial in sending and receiving order (all that is required is the article name and total number).

As seen above, the method for preparing impression taking and molding materials and the dental diagnosing/treating chemical materials used in the method according to the present invention, can exhibit the following advantages because measurement of chemical material powder is unnecessary:

(1) Simple in handling of the materials and therefore, time is saved.

(2) Since material powder cannot fly off in different directions, the examination room can be kept clean.

(3) No powder loss occurs.

(4) Since material powder is previously wrapped in an accurate quantity, an accurate mixture ratio between the powder and water can be obtained, thus improving the impression taking or molding accuracy.

(5) Hygienical management of the material powder is easy.

DESCRIPTION OF THE PREFERRED EMBODIMENT

Figure 1:
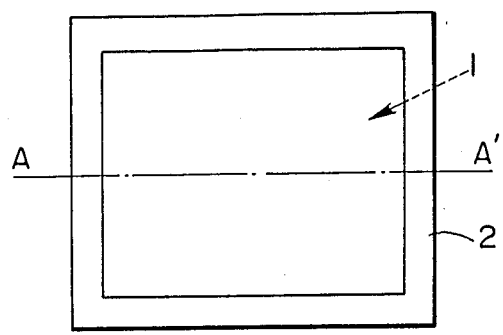
FIGS. 1a and 1b show a plan view and a sectional view taken along line A—A' in FIG. 1a, of an embodiment of dental diagnosing/treating chemical material in pack used in a method of preparing dental taking and molding materials according to the present invention.
Figure 1:
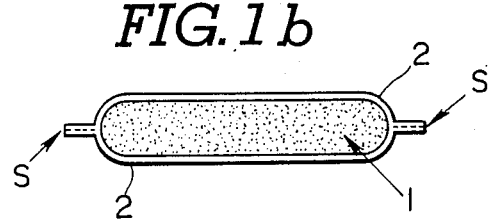

Referring to FIG. 1, material powder 1 may comprise alginic acid salt for dental use, dental plaster, a mixture of carboxylic acid polymer and aluminosilicate or dental cement, and a predetermined quantity of such chemical material powder is wrapped with water-soluble film 2 to form a single sealed pack. During the wrapping operation, the water-soluble films 2 are bonded or heat sealed at its junction part S. The materials thus wrapped are easy in handling in shipping from factory to users because they are transported in containers such as boxes or bags. Further, an impression taking or molding material can be readily prepared merely by immersing a desired number of packs in a prescribed quantity of water as they are without opening them, and then mixing an kneading them.

In practical applications, the chemical material powder 1 is wrapped by the earlier-mentioned two methods.

More specifically, in the first method, plural types of packs which contain different quantity of chemical material powder respectively corresponding to the quantity required for the respective clinical treatments are prepared. Where the chemical material powder 1 is alginate impression material (alginate acid salt), three types of packs, i.e., 21, 14 and 7 gram packs, are prepared, because 21, 14 and 7 grams of alginate material are required for 1, ½ jaw and 2-3 teeth respectively, as described earlier. A dentist or a dental mechanic can quickly prepare a desired impression taking material by selecting a pack containing an amount necessary for the clinical treatment concerned and putting the pack into a proper quantity of water, and subsequently mixing and kneading them.

In the second method, a single type of pack is prepared in which the unit quantity of the powder is contained. Where alginate impression material is used as the chemical material 1 for example, the pack contains unit quantity of 7 grams of alginate material.

When it is desired to take an impression corresponding to 1 or ½ jaws, the user use 3 or 2 packs. This is remarkably simple and convenient when compared with the conventional method. Further, this method is advantageous as described earlier.

Figure 2:
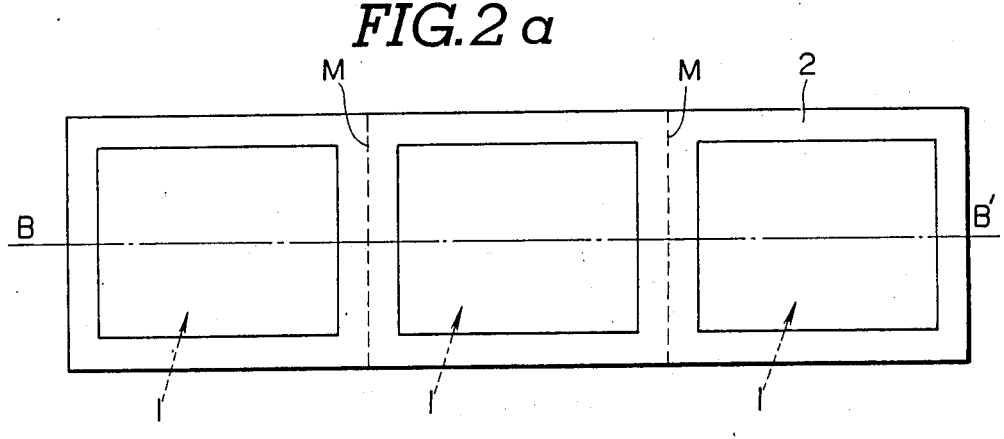
FIGS. 2a and 2b show plan and sectional views of another embodiment of the chemical material.
Figure 2:
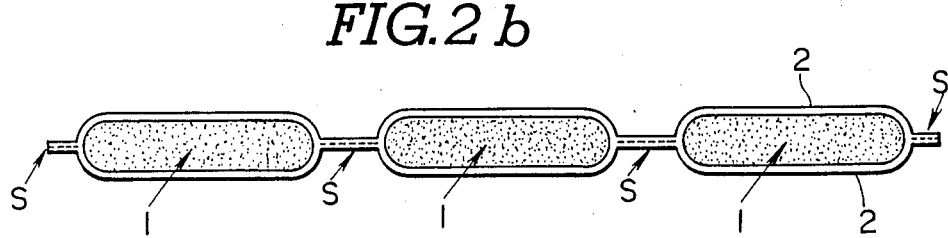

FIG. 2 shows another embodiment of a pack of the chemical material powder 1 suitably employed especially in the second method.

More in detail, when alginate impression material is used as the chemical material power 1, it is determined that the unit wrapping quantity of alginate material is 7 grams. Then, 2 packs (corresponding to 14 grams) and 3 racks (corresponding to 21 grams) are required for ½ and 1 jaw respectively. In FIG. 2, 3 packs are connected with a line of perforations M being provided in each connecting portion between packs.

While the present invention has been described in the cases where the material powder 1 is packed with the water-soluble film 2 in such manners as shown in FIGS. 1 and 2, it should be understood that the invention is not limited only to the particular embodiments shown but rather to cover any packing manner so long as a predetermined amount of the material powder 1 can be packed successively. Further, although polyvinyl alcohol (PVA), polysaacharide, gelatine and cellulose have been enumerated as a material of the water-soluble film 2, any other material may be selected so long as it has no inferior effect both on human body and on the properties of the impression taking or molding material.

What is claimed is:

1. A method of preparing an impression taking material for use in dental treatment by kneading with a proper amount of water a desired quantity of powder of alginic acid salt which becomes plastic when mixed with water, which comprises using one package of said powder selected from a plural types of packages of water-soluble film each containing said powder whose quantity corresponds to respective dental treatment.

2. A method of preparing an impression taking material for use in dental treatment by kneading with a proper amount of water a desired quantity of powder of alginic acid salt which becomes plastic when mixed with water, which compresses using a required number of packages of a water-soluble film containing said powder of minumum quantity required among every dental treatment, said required number being determined corresponding to dental treatment to be carried out.

3. An impression taking material for use in dental treatment comprising a powder of alginic acid salt having a property of becoming plastic when mixed with water and subsequently hardening with time, wherein said powder is of a quantity required for one impression taking which is packed in a water soluble film.

4. An impression taking material for use in dental treatment comprising a powder of alginic acid salt having a property of becoming plastic when mixed with water and subsequently hardening with time, wherein said powder is of minimum unit, an integral multiple of which is a required amount for each impression taking, which is packed in a water soluble film.

5. The impression taking material as set forth in claim 4, wherein there are provided a plurality of said packed powder of a minimum unit, which are connected to each other.

6. The impression taking material as set forth in claim 5, wherein a line of perforations is provided in each connecting portion between said powder packs of a minimum unit.

7. An impression taking material for use in dental treatment comprising a powder of alginic acid salt having a property of becoming plastic when mixed with water and subsequently hardening with time, wherein said powder of a maximum quantity for very impression taking is packed in a water-soluble film package, said package being provided with a partitioning section for dividing said powder of maximum quantity into a plurality of minimum quantity units for every impression taking, an integral multiple of said minimum quantity units being a required quantity for each impression taking.

8. The impression taking material as set forth in claim 7, wherein said maximum quantity is a quantity required for impression taking of one jaw and said minimum quantity unit is one third of said maximum quantity.

9. The impression taking material as set forth in claim 7, wherein said partitioning section is provided with a line of perforations.

* * * * *